US00PP16082P2

(12) United States Plant Patent
Stroet

(10) Patent No.: US PP16,082 P2
(45) Date of Patent: Nov. 1, 2005

(54) ***PORTULACA* PLANT NAMED 'PINK PANTHER'**

(50) Latin Name: *Portulaca grandiflora*
Varietal Denomination: Pink Panther

(76) Inventor: Theodorus B. J. Stroet, Gildestraat 225, 2671 BW Naaldwijk (NL)

( * ) Notice: Subject to any disclaimer, the term of this patent is extended or adjusted under 35 U.S.C. 154(b) by 56 days.

(21) Appl. No.: 10/888,831

(22) Filed: Jul. 9, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Portulaca* plant named 'Pink Panther', characterized by its outwardly spreading and trailing plant habit; freely branching growth habit; relatively rapid growth rate; double flower form; and pink-colored flowers.

1 Drawing Sheet

Botanical classification/cultivar designation: *Portulaca grandiflora* cultivar Pink Panther.

BACKGROUND OF THE INVENTION

The present Invention relates to a new and distinct cultivar of *Portulaca* plant, botanically known as *Portulaca grandiflora,* and hereinafter referred to by the name 'Pink Panther'.

The new *Portulaca* is a product of a planned breeding program conducted by the Inventor in Naaldwijk, The Netherlands. The objective of the breeding program is to create new *Portulacas* with interesting flower forms and flower colors.

The new *Portulaca* is a naturally-occurring whole plant mutation of an unnamed selection of *Portulaca grandiflora,* not patented, that was discovered and selected by the Inventor during the summer of 2001 in a controlled environment in Naaldwijk, The Netherlands, on the basis of its pink-colored double flowers.

Asexual reproduction of the new cultivar by cuttings in a controlled environment in Naaldwijk, The Netherlands since 2001, has shown that the unique features of this new *Portulaca* are stable and reproduced true to type in successive generations.

SUMMARY OF THE INVENTION

Plants of the cultivar Pink Panther have not been observed under all possible environmental conditions. The phenotype may vary somewhat with variations in environment and culture such as temperature, light intensity, and daylength without, however, any variance in genotype.

The following traits have been repeatedly observed and are determined to be the unique characteristics of 'Pink Panther'. These characteristics in combination distinguish 'Pink Panther' as a new and distinct cultivar:

1. Outwardly spreading and trailing plant habit.
2. Freely branching growth habit.
3. Relatively rapid growth rate.
4. Double flower form.
5. Pink-colored flowers.

Plants of the parent selection differed primarily from plants of the new *Portulaca* in flower form and coloration as plants of the parent selection had single orange and yellow-colored flowers. In addition, plants of the new *Portulaca* is more vigorous than plants of the parent selection.

Plants of the new *Portulaca* can be compared to plants of the *Portulaca* cultivar Cindy, disclosed in U.S. Plant Pat. No. 13,605. In side-by-side comparisons conducted in Naaldwijk, The Netherlands, plants of the new *Portulaca* differed from plants of the cultivar Cindy primarily in flower coloration as plants of the cultivar Cindy had yellow and orange bi-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproduction of this type. Colors in the photographs may differ slightly from the color values cited in the detailed botanical description which accurately describe the colors of the new *Portulaca.*

The photograph at the top of the sheet comprises a side perspective view of a typical flowering plant of 'Pink Panther'.

The photograph at the bottom of the sheet comprises a close-up view of a typical flower of 'Pink Panther'.

DETAILED BOTANICAL DESCRIPTION

Plants used for the aforementioned photgraphs and following observations and measurements were planted into 15-cm containers and grown for about four months during the fall in a glass-covered greenhouse in Aalsmeer, The Netherlands. During the production of the plants, the day and night temperatures averaged 20° C.

In the following description, color reference are made to The Royal Horticultural Society Colour Chart, Edition 1995, except where general terms of ordinary dictionary significance are used.

Botanical classification: *Portulaca grandiflora* cultivar Pink Panther.

Parentage: Naturally-occurring whole plant mutation of an unnamed selection of *Portulaca grandiflora,* not patented.

Propagation:

*Type.*—By cuttings.

*Time to initiate roots.*—About 12 days at 20° C.

*Root description.*—Fine, freely branching.

Plant description:

*Form.*—Outwardly spreading and trailing plant habit. Freely branching with lateral branches potentially developing at every node without pinching.

*Growth rate.*—Relatively rapid; about eight weeks are required to produce a finished flowering plant in a 10-cm container.

*Plant height.*—About 15 cm.

*Plant diameter.*—About 50 cm.

*Lateral branches.*—Length: About 20 to 35 cm. Diameter: About 3 mm. Internode length: About 1 to 3.5 cm. Strength: Strong. Texture: Smooth, glabrous. Color: 144B.

*Foliage description.*—Arrangement: Alternate, simple. Length: About 1 to 3 cm. Width: About 4 to 10 mm. Shape: Oblong to ovate. Apex: Rounded. Base: Obtuse. Margin: Entire. Texture, upper and lower surfaces: Smooth, glabrous; fleshy. Venation pattern: Pinnate. Petiole length: About 1 to 2 mm. Petiole diameter: About 1 mm. Color: Developing foliage, upper surface: 137B. Developing foliage, lower surface: 137C. Fully expanded foliage, upper surface: 137A. Fully expanded foliage, lower surface: 138B. Venation, upper and lower surfaces: 137C. Petiole, upper and lower surfaces: 146D.

Flower description:

*Flower type and habit.*—Numerous double rotate flowers; solitary or in clusters. Flowers face upright or outward. Freely flowering with about 20 to 40 flowers and flower buds per lateral branch. Flowers not persistent.

*Time to flower.*—Early flowering, plants begin to flower about six weeks after planting.

*Natural flowering season.*—In the northern hemisphere, plants flower during the summer and autumn; flowering recurrent during this period.

*Flower longevity on the plant.*—About three days.

*Fragrance.*—None detected.

*Flowers.*—Diameter: About 2.3 cm. Depth (height): About 1 cm.

*Flower buds.*—Length: About 4 to 6 mm. Diameter: About 2 to 4 mm. Shape: Roughly ovoid. Color: 146C.

*Corolla.*—Arrangement/appearance: Five petals in a single whorl, surrounding 30 to 40 petaloids which are transformed stamens and pistils. Petal length: About 1.2 to 1.5 cm. Petal width: About 4 to 10 mm. Petal shape: Obovate. Petal apex: Cuspidate. Petal base: Obtuse. Petal margin: Entire. Petal texture, upper and lower surfaces: Smooth, satiny. Petal color: When opening, upper and lower surfaces: 76D. Fully opened, upper and lower surfaces: 76D. Petaloid length: About 5 to 11 mm. Petaloid width: About 2 to 3 mm. Petaloid shape: Oblanceolate. Petaloid apex: Acute. Petaloid base: Acuminate. Petaloid margin: Entire. Petaloid texture: Smooth, satiny. Petaolid color, upper and lower surfaces: Towards apex: 76C. Mid-section: 84C. Towards base: 76C.

*Calyx.*—Appearance: Two-cleft. Length: About 5 to 6 mm. Diameter: About 3 to 4 mm. Shape: Deltoid. Apex: Acute. Base: Cuneate. Texture, upper and lower surfaces: Smooth, glabrous. Color, upper and lower surfaces: 146D.

*Peduncles.*—Length: About 2 to 3 mm. Diameter: About 1 to 2 mm. Strength: Strong. Angle: Mostly erect. Texture: Smooth, glabrous. Color: 144A.

*Reproductive organs.*—No stamens or pistils observed; reproductive organs transformed into petaloids.

*Seed/fruit.*—Seed nor fruit production has not been observed.

Disease/pest resistance: Plants of the new *Portulaca* have not been noted to be resistant to pathogens or pests common to *Portulaca.*

It is claimed:

1. A new and distinct cultivar of *Portulaca* plant named 'Pink Panther', as illustrated and described.

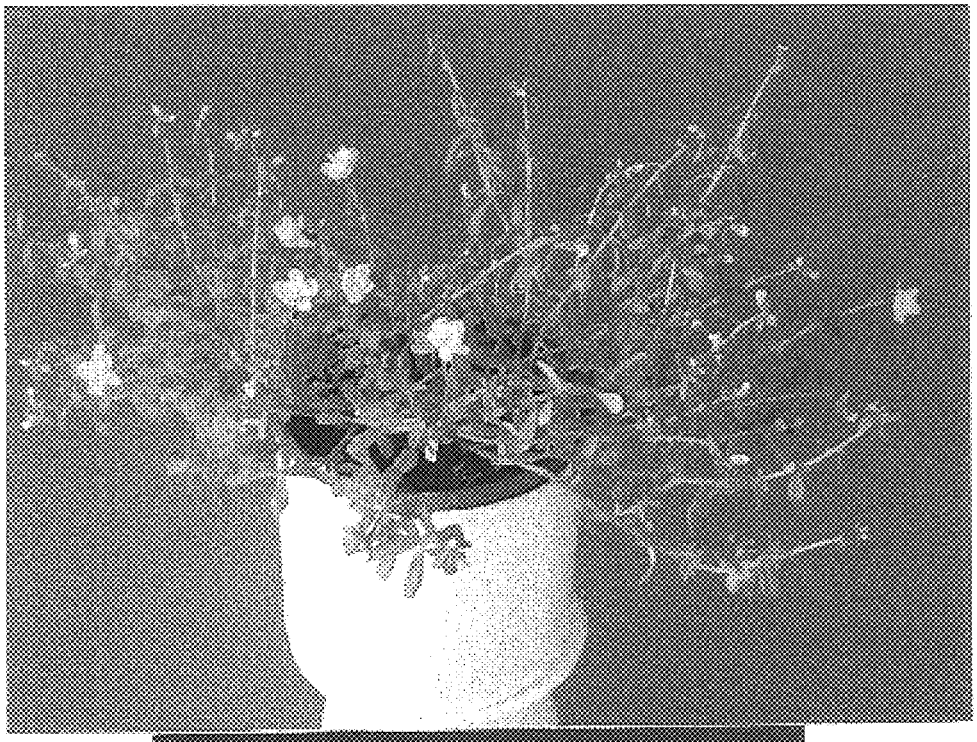
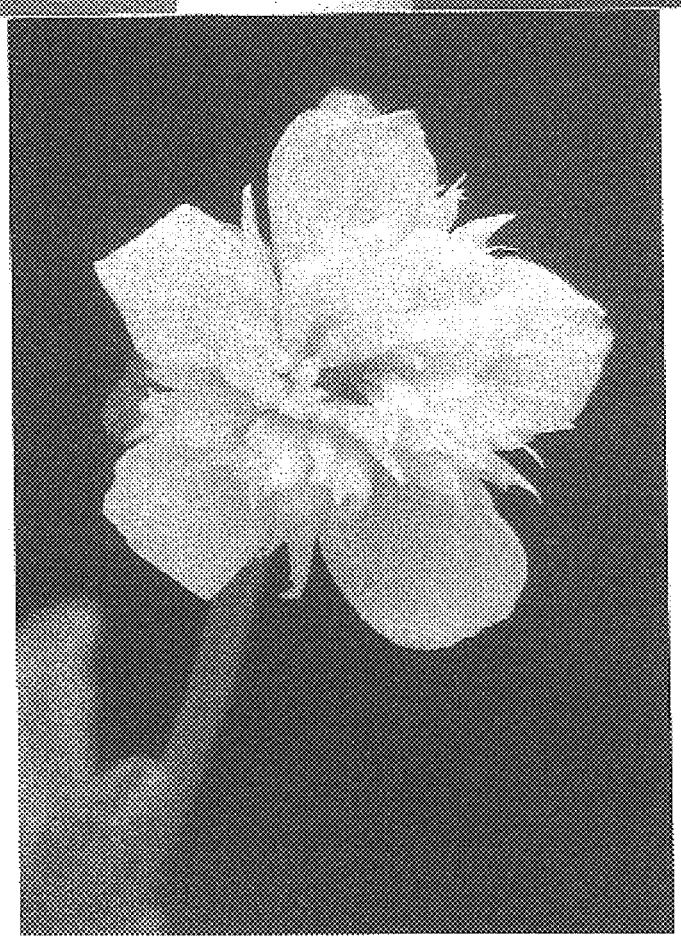

* * * * *